DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED MARCH 27, 1973

908 O.G. 788

T908,001

INHIBITING POLYMERIZATION OF ACRYLIC AND METHACRYLIC ACIDS AND ESTERS THEREOF

John E. Besser, 4422 Harbor Drive, Kingsport, Tenn. 37662

Filed Feb. 14, 1971, Ser. No. 118,506
Int. Cl. C07c *69/54*
U.S. Cl. 260—486 R
No Drawing. 12 Pages Specification

Undesired polymerization of acrylic and methacrylic acids and esters thereof can be prevented by adding thereto from about 200 to about 20,000 parts per million by weight of at least one 2,5-di-substituted alkylhydroquinone having the general formula:

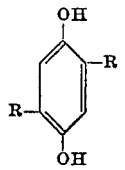

wherein R is an alkyl radical of from four to five carbon atoms. The 2,5-di-substituted alkylhydroquinone may be added either directly to the acrylic and methacrylic acids and esters thereof or to the reaction mixture from which the acids and esters are prepared. When these substituted alkylhydroquinones are added to the reaction mixture it has been found that they not only effectively prevent polymerization of the acid or ester during the synthesis process, but also remain in the synthesized products thereby effectively inhibiting their polymerization during storage. The substituted alkylhydroquinones polymerization inhibitors of this invention do not contribute any undesirable color or in any way interfere with successful subsequent processing of the acids or esters into any desired ultimate product.